United States Patent [19]

Azcona et al.

[11] Patent Number: 5,530,008
[45] Date of Patent: Jun. 25, 1996

[54] USE OF 5-HT₃ RECEPTOR ANTAGONISTS IN TREATING PANIC DISORDERS OR OBSESSIVE COMPULSIVE DISORDERS

[75] Inventors: Alberto E. Azcona; Pamela Taylor, both of Basel, Switzerland

[73] Assignee: Sandoz Ltd., Basel, Switzerland

[21] Appl. No.: 187,413

[22] Filed: Jan. 24, 1994

Related U.S. Application Data

[63] Continuation of Ser. No. 635,156, filed as PCT/EP90/00540, Apr. 6, 1990, abandoned.

[30] Foreign Application Priority Data

Apr. 21, 1989 [GB] United Kingdom ............ 8909147
Jul. 20, 1989 [GB] United Kingdom ............ 8916602

[51] Int. Cl.⁶ ................ A61K 31/44; A61K 31/47; A61K 31/415
[52] U.S. Cl. ............ 514/304; 514/299; 514/300; 514/306; 514/307; 514/397
[58] Field of Search ............... 514/289, 299, 514/300, 304, 307, 306, 397

[56] References Cited

U.S. PATENT DOCUMENTS 5,187,164 2/1993 Hansen ................... 514/299

FOREIGN PATENT DOCUMENTS

| | | |
|---|---|---|
| 99194 | 1/1984 | European Pat. Off. . |
| 306323 | 3/1989 | European Pat. Off. . |
| 329904 | 8/1989 | European Pat. Off. . |
| 3740984 | 6/1989 | Germany . |
| 2193633 | 2/1988 | United Kingdom . |

OTHER PUBLICATIONS

Medline Abst. 89005374, of Paper "Similar effects of diazepam and the 5HT3 receptor antagonist ICS 205–930 on place inversion" *Eur. J. Pharmacol.* 151(2): 321–4 (1988, Jul. 7).
Merck Manual, Berkow ed, Merck Sharp & Dohme Research Lab, pp. 1441–1443 1987.
Biol. Psychiatry, vol. 20, pp. 1174–1188 (1985).
Psychopharmacology Bull., vol. 24, pp. 370–374 (1988).
Br. J. Pharmacol., vol. 93, pp. 985–993 (1988).
Eur. J. Pharmacol., vol. 151, No. 2, pp. 321–324 (1988).
Br. J. Pharmacol., vol. 92, Suppl., p. 657P (1987).
Br. J. Pharmacol., vol. 94, Proc. Suppl., p. 314P (1988).
Neuroscience Letters Suppl., vol. 32, p. S44 (1988).
General Pharmacol., vol. 19, No. 3, pp. 347–356 (1988).
Advances in Biol. Psych., vol. 17, pp. 84–99 (1988).
New England Jour. of Medicine, vol. 321, No. 8, pp. 539–541 (1989).
Psychopharm. Bull., vol. 23, No. 1, pp. 145–149 (1987).
Inter. Clin. Psych., vol. 2, pp. 33–45 (1987).
The Merck Manual of Diagnosis and Therapy, 14th Edition, R. Berkow, pp. 1439–1443 (1982).
Reviews in the Neuro., vol. 2, No. 1, pp. 41–65 (1988).
Adv. Biochemical Psycho., vol. 14, pp. 29–44 (1975).

*Primary Examiner*—Raymond Henley, III
*Attorney, Agent, or Firm*—Robert S. Honor; Melvyn M. Kassenoff; Joseph J. Borovian

[57] ABSTRACT

5-HT₃ Receptor antagonists are useful in treating panic disorders or obsessive compulsive disorders.

8 Claims, No Drawings

USE OF 5-HT₃ RECEPTOR ANTAGONISTS IN TREATING PANIC DISORDERS OR OBSESSIVE COMPULSIVE DISORDERS

This is a continuation of application Ser. No. 07/635,156, filed Dec. 19, 1990 now abandoned, which is a 371 of International Application No. PCT/EP90/00540, filed on Apr. 6, 1990.

The present invention relates to a new use, in particular a new pharmaceutical use, for the compound group comprising 5HT₃ receptor antagonists, said compound group being referred to hereinafter collectively as COMPOUNDS OF THE INVENTION.

5-HT₃ receptor antagonists are a well known class of compounds. Spatial models for 5-HT₃ receptors and 5-HT₃ antagonists have been proposed recently by M. F. Hibert and S. Peroutka. They are typically compounds which act on 5-HT₃ receptors on the e.g. isolated rabbit heart or vagus nerve by antagonizing the action of 5-HT thereon. They may have a pA₂ greater than 6 or preferably more than 8 or 9.5-HT₃ antagonists may be selective for 5-HT₃ receptors as compared to other serotonin receptors or dopamine receptors.

Preferred 5-HT3 antagonists include a) ICS 205-930, having the chemical name indol-3-yl carboxylic acid endo-8-methyl-8-aza-bicyclo [3.2.1] oct-3-yl ester b) GR 38032 F, also known as ondansetron, having the chemical name 1,2,3,9-tetrahydro-9-methyl-3-[(2-methyl-1H-imidazol-1-yl) methyl]-4H-carbazol-4-one c) BRL 43694, also known as granisetron, having the chemical name 1-methyl-indazol-3-yl carboxylic acid 9-methyl-9-aza-bicyclo[3.3.1]non-3a-yl amide, d) zacopride, in optically active form, preferably the R (+) form or in racemic form, e) MDL 73147, also known as trans-hexahydro-8-(3-indolylcarbonyloxy)- 2,6-methano-2H-quinolizin-3(4H)one, f) benzo[b]thien-7-yl carboxylic acid endo-8-methyl-8-azabicyclo[3.2.1oct-3-yl ester, known from e.g. EP 294,292, g) GR 65630 also known as 3-(5-methyl-1H-imidazol-4-yl)-1-(1-methyl- 1H-indol-3-yl)-1-propanone, h) GR 68755, j) LY 278,584 also known as 1-methyl-indazol-3-yl carboxylic acid endo-8-methyl-8-aza-bicyclo[3.2.1oct-3-yl amide, k) GR 67330 also known as 1,2,3,9-tetrahydro-9-methyl-3-(5-methyl- 1H-imidazol-4-yl)methyl-4H-carbazol-4-one, and l) a compound chosen from the following:

i) 2,3,4,5-tetrahydro-5-(phenylmethyl)-2-[(5-methyl-1H-imidazol- 4-yl)methyl]-1H-pyridol[4,3,-b]indol-1-one, 5-cyclopentyl-2,3,4,5-tetrahydro-2-[(5-methyl-1H-imidazol- 4-yl)methyl]-1H-pyridol[4,3-b]indol-1-one, 2,3,4,5-tetrahydro-2-[(5-methyl-1H-imidazol-4-yl)methyl- 5-propyl-1H-pyridol[4,3-b]indol-1-one, 5-(cyclopentylmethyl)-2,3,4,5-tetrahydro-2-[(5-methyl-1H-imidazol-4-yl)methyl-1H-pyrido[4,3-b]indol-1-one, 3,4,5,6-tetrahydro-6-methyl-2-[(5-methyl-1H-imidazol-4-yl)methyl-azepino[ 4,3-b]indol-1-(2H)-one, 2,3,4,5-tetrahydro-N,N-dimethyl-2-[(5-methyl-1H-imidazol- 4-yl)methyl-1-oxo-5H-pyrido[4,3-b]indol-5-carboxamide, 2,3,4,5-tetrahydro-2-[(5-methyl-1H-imidazol-4-yl)methyl- 5-(2-propynyl)-1H-pyridol[4,3-b]indol-1-one, and any other compound falling under the scope of EP 306,323, the contents of which are incorporated herein by reference, ii) 3-(5-methyl-1H-imidazol-4-yl)-1-(1-naphthalenyl)-1-propanone, 1-(4-methoxy-1-naphthalenyl)-3-(5-methyl-1H-imidazol-4-yl)-1-propanone, 1-(2-hydroxy-1-naphthalenyl)-3-(5-methyl-1H-imidazol-4-yl)-1-propanone, 1-(benzo[b]thien-3-yl)-3-(5-methyl-1H-imidazol-4-yl)-1-propanone, 3-(5-methyl-1H-imidazol-4-yl)-1-(1-methyl-1H-indazol-3-yl)- 1-propanone, or 3-(5-methyl-1H-imidazol-4-yl)-1-(1-methyl-1H-indol-4-yl)- 1-propanone, and any other compound falling under the scope of EP 291,172, the contents of which are incorporated herein by reference, iii) 1,2,3,9-tetrahydro-3-((1H-imidazol-2-yl)methyl-9-methyl- 4H-carbazolone, and 3-(1H-imidazol-2-yl)-1-(1-methyl-1H-indole-3-yl)-1-propanone, and any other compound falling under the scope of EP 307,145 the contents of which are incorporated herein by reference, iv) 3-(5-methyl-1H-imidazol-4-yl)-1-(1,7-dimethyl-1H-indol- 3-yl)propanone, and any other compound falling under the scope of EP 276,163 the contents of which are incorporated herein by reference, v) 3-(5-methyl-1H-imidazol-4-yl)-1-(1-methyl-1H-indol-3-yl)- 1-propanone, 3-(5-methyl-1H-imidazol-4-yl)-1-(1,2-dimethyl-1H-indol- 3-yl)-1-propanone, 2,3-dimethyl-3-(5-methyl-1H-imidazol-4-yl)-1-(1-methyl- 1H-indol-3-yl)-1-propanone, and any other compound falling under the scope of EP 242,973A, the contents of which are incorporated herein by reference, vi) a compound specifically or generically disclosed in DE 3,740,352 A, WO 8803801 A, EP 266,899 A, GB 2,192,885 A, GB 2,208,862 A, EP 219,929 A, EP 219,193 A, EP 212,398 A, EP 210,840 A, EP 191,562 A, EP 248,843 A, WO 89/09217, the contents of which are incorporated herein by reference.

vii) a compound generically or specifically disclosed in any of the following patent applications or foreign equivalents thereof, GB 8805268/88; GB 8805269/88; GB 8804107/88; GB 8816550/88; GB 8804104/88; GB 8804422/88; GB 8729823/87; GB 8729596/87; GB 8729597/87; GB 8726586/87; GB 8821179/88;

the contents of which are incorporated herein by reference, viii) N,1-dimethyl-7-fluoro-N-[(5-methyl-1H-imidazol-4-yl)methyl]-1H-indole-3-carboxamide, N,1-dimethyl-N-[(5-methyl-1H-imidazol-4-yl)methyl]- 1H-indole- 3-carboxamide, and any other compound falling under the scope of EP 347,229 A, the contents of which are incorporated herein by reference, ix) 1-amino-5a,6,7,8,9,9a-hexahydrodibenzofuran-4-(N-1-azabicyclo-[2.2.2.]oct-3-yl)carboxamide, 2-chloro-5a,6,7,8,9,9a-hexahydrodibenzofuran-4-(N-1-azabicyclo-[2.2.2.]oct-3-yl)carboxamide, 1-amino-2-chloro-5a,6,7,8,9,9a-hexahydrodibenzofuran-4-(N-1-azabicyclo-[2.2.2.]oct-3-yl)carboxamide, 2-chloro-cis-5a,6,7,8,9,9a-hexahydrodibenzofuran- 4-(N-1-azabicyclo- [2.2.2.]oct-3-yl)carboxamide, 2-chloro-cis-5aS,6 ,7,8,9,9aS-hexahydrodibenzofuran-4-(N-1-azabicyclo- [2.2.2.]oct-3S-yl)carboxamide, 2-chloro-cis-5aS,6 ,7,8,9,9aS-hexahydrodibenzofuran-4-(N-1-azabicyclo- [2.2.2.]oct-3R-yl)carboxamide, 2-chloro-cis-5aR,6 ,7,8,9,9aR-hexahydrodibenzofuran-4-(N-1-azabicyclo-[2.2.2.]oct-3S-yl)carboxamide, 2-chloro-cis-5aR,6 ,7,8,9,9aR-hexahydrodibenzofuran-4-(N-1-azabicyclo- [2.2.2.]oct-3R-yl)carboxamide, 2-chloro-trans-5a,6,7,8,9,9a-hexahydrodibenzofuran-4-(N-1-azabicyclo-[2.2.2.]oct-3-yl)carboxamide, and any other compound falling under the scope of EP 339,950 A, the contents of which are incorporated herein by reference, x) 5,6,9,10-tetrahydro-10-[(5-methyl-1H-imidazol-4-yl)methyl]-4H-pyrido[3,2,1-j,k]carbazol-11(8H) -one, and any other-compound falling under the scope of EP 344,015 A, the contents of which are incorporated herein by reference, xi) 3,4-dihydro-2-[(5-methyl-1H-imidazol-4-yl)methyl]-1(2H)-dibenzofuranone, 3,4-dihydro-2-[(5-methyl-1H-imidazol-4-yl)methyl]-1(2H)-dibenzothiophenone, 6,7,8,9-tetrahydro-5-methyl-9-[(2-methyl-1H-imidazol-1-yl)methyl]-cyclohept[b]indol-10(5H)-one, and any other compound falling under the scope of EP 317,088 A, the contents of which are incorporated herein by reference, xii) 3,4-dihydro-2-[(5-methyl-1H-imidazol-4-yl)methyl]-benzofuro[3,2-c]pyridin-1(2H)-one, 3,4-dihydro-2-[(5-methyl-1H-imidazol-4-yl)methyl]-[1]benzothieno-[3,2-c]pyridin-1(2H)-one, and any other compound falling under the scope of EP 339,959 A, the contents of which are incorporated herein by reference, xiii) 1,2-dihydro-3-[(5-methyl-1H-imidazol-4-yl)methyl]-4(3H)-phenanthrenone, 3,4-diyhdro-2-[(5-methyl-1H-imidazol-4-yl)methyl]-benz[h]isoquinolin-1(2H)-one, and any other compound falling under the scope of EP 336,759 A, the contents of which are incorporated herein by reference, and xiv) 1-(5,6-dihydro-4H-pyrrolo[3,2,1-i,j]quinolin-1-yl)-3-(5-methyl- 1H-imidazol-4-yl)-1-propanone, and any other compound falling under the scope of EP 327,307 A, the contents of which are incorporated herein by reference.

5-HT$_3$ receptor antagonists have been shown to be effective in relieving the pain induced by serotonin applied to a blister base on the human forearm.

5-HT$_3$ receptor antagonists have been disclosed for treatment of a variety of diseases, for example vomiting, especially chemotherapy induced emesis and other gastrointestinal disorders, nausea and arrhythmia.

5-HT$_3$ antagonists are indicated for the treatment of anxiety on the basis of tests with rodents, e.g. rats and mice. In GB 2193633/A we have described the effects of 5-HT$_3$ antagonists on rodents such as rats and mice, and it was stated that 5-HT$_3$ antagonists were indicated in the treatment of stress related psychiatric disorders, including stress-induced social phobias.

A review of rodent experiments has been published by B. Costall et al., Reviews in the Neurosciences, 1988, Vol. 2., No. 1, p. 41 et seq, particularly from p. 50 to 54.5-HT$_3$ antagonists were said to mimic the anxiolytic activity seen with diazepam, but they lacked the sedative/muscle relaxant component, they were ineffective in the commonly used water lick conflict test, and they lacked the withdrawal anxiogenesis. It was postulated that 5-HT$_3$ antagonists would be a novel series of anxiolytic agents which do not have the disadvantages of benzodiazepines. Little has been published, however, on the clinical trials of 5-HT$_3$ antagonists in anxiety.

In accordance with the present invention it has now surprisingly been found that 5-HT$_3$ antagonists are especially useful in the treatment of anxiety disorders other than directly stress-induced anxiety disorders, particularly panic disorders (also known as panic attacks), and agoraphobia.

Panic disorders and agoraphobia are specifically classified anxiety disorders according to the DSM-III-R, the Diagnostic and Statistical Manual of Mental Disorders, 3rd Edition - Revised, published by the American Psychiatric Association, Washington, DC, USA in 1987, pages 235 to 241, the contents of which are incorporated herein by reference, and do not depend on stress. They are classified separately from other anxiety disorders, namely social phobias, simple phobias, post-traumatic stress disorders, generalized anxiety disorders.

Panic disorders have a distinctive pathophysiology and a familial genetic pattern of interested risk. In panic disorders there is typically completely unstimulated "herald" attack. The attacks however recur. The patient often suffers from anticipatory anxiety fearing the onset of another attack.

The basic clinical features of panic disorders are recurrent attacks of panic (e.g. 3 attacks within a 3-week period) in circumstances excluding life-threatening conditions or marked physical exertion.

The attack is experienced by the patient as a sudden surge of intense apprehension, fear or terror. Some patients emphasize "a terror of fainting, collapsing, dying, suffering a life-threatening disease or losing control". This sudden attack should be associated with at least 3 or 4 out of the 14 classical autonomic symptoms usually reported by the patients:

SYMPTOMS ASSOCIATED WITH PANIC ATTACKS
1. Shortness of breath (dyspnoea)
2. Choking/smothering feeling
3. Palpitations/tachycardia
4. Chest pain/discomfort
5. Sweating
6. Faintness
7. Dizziness/light headedness/unsteadiness
8. Nausea/abdominal distress
9. Depersonalization/derealization
10. Tingling sensation/paresthesia
11. Hot flushes/cold chills
12. Trembling/shaking
13. Fear of dying
14. Fear of going mad/losing control These symptoms occur within 10 minutes of the onset of the attack. The symptoms which characterized the attack are usually interpreted as suggestive of autonomic arousal. Sometimes patients may also report striking cognitive symptoms or impressions "of going mad".

Generally, no warning sign precedes the panic attack. Some attacks occur unexpectedly, whereas others are situational. The patient with panic disorder usually fears particular situations such as going into a supermarket, a stadium, or using public transport.

But patients are often able to get through these particular situations without inducing an attack. In other conditions, however, the patient may suffer an attack for no apparent reason or in a situation not previously linked with such episodes.

The biological substrate leading to the occurrence of a panic attack is still unknown. The "trigger" factors either physiological (i.e. a place, a supermarket) or psychological induce a "neurochemical storm" within different brain structures leading to the appearance of fears or terror and also to the autonomic signs.

Moreover, the appearance of panic disorders in a given patient leads to the development of anticipatory anxiety (i.e. the fear of further attacks). Avoidance (or phobic) and/or dependence (e.g. requiring companion to enter a supermarket) behaviours develop in response to anticipatory anxiety. Such avoidance behavior, resulting of an adaptative response to attack, becomes a major feature of patients with agoraphobia. Therefore, the therapeutic strategy should also include an appropriate approach of the avoidance behavior and not consider only the treatment attacks.

The invention is of particular use for patients suffering from panic disorder with agoraphobia (DSM-III-R Classification 300.01), panic-disorder without agoraphobia (DSM-III-R Classification 300.21) or agoraphobia without history of panic disorder (DSM-III-R Classification 300.22), especially for panic disorders.

Agoraphobia is also regarded as being separate from other anxiety disorders (see for example page 1181 of Chapter 121 from Psychopharmacology: The Third Generation of Progress edited by Herbert Y. Meltzer, Raven Press, New York 1987).

The use of 5-HT$_3$ antagonists in treating panic attacks is even more surprising since the typic anxiolytic diazepam is relatively ineffective against panic attacks.

The use in agoraphobia could not be predicted from the art, e.g. in GB 2,193,633 A inter alia no open field experiments were done e.g. with animals alone in a large enclosure.

In accordance with the particular findings of the present invention, the present invention provides in a first aspect:

1 A method of treating a subject suffering from or prone to panic disorders and/or agoraphobia, which comprises administering to a subject in need of such treatment a therapeutically effective amount of a 5-HT$_3$ receptor antagonist.

In a series of specific or alternative embodiments, the present invention also provides:

1.1. A method of treating a subject suffering from or prone to panic disorders without agoraphobia which comprises administering to a subject in need of such treatment a therapeutically effective amount of a 5-HT$_3$ receptor antagonist.

1.2. A method of treating a subject suffering from or prone to panic disorders with agoraphobia, which comprises administering to a subject in need of such treatment a therapeutically effective amount of a 5-HT$_3$ receptor antagonist.

1.3 A method of treating a subject suffering from or prone to agoraphobia, which comprises administering to a subject in need of such treatment a therapeutically effective amount of a 5-HT$_3$ receptor antagonist.

The effect of 5-HT$_3$ antagonists in the treatment of panic disorders is observed in e.g. clinical trials using for example a representative compound such as ICS 205-930 in patients suffering from agoraphobia and especially panic disorders.

TRIAL A

This study is designed as an open-label trial with ICS 205-930 in patients with panic attacks and/or agoraphobia, and panic attacks with or without agoraphobia.

Design of the Study

The patients were in- and outpatients with anxiety disorders. They were carefully diagnosed and classified according DSM-III criteria. During the screening phase, physical, psychiatric, laboratory and ECG evaluations were conducted. They were repeated at the end of treatment.

The patients received initially 1 mg/day ICS 205-930 during 3 days. Further dose increases (5, 10, 15 and 30 mg/day) were made at 3–4 day intervals if neither positive nor adverse effects appeared.

If changes in anxiety, mood or behavior were noticed, and the investigator considered that they could be attributed to ICS 205-930, a single-blind, placebo-controlled phase of 3–4 days was intercalated.

Results

| Pt.Nr. | Sex | Age | Diagnosis | Responder |
|---|---|---|---|---|
| 1 | M | 40 | Agoraphobia/Panic attacks | Yes |
| 2 | M | 32 | Panic attacks | Yes |
| 3 | F | 41 | Panic attacks | Yes |
| 4 | F | 24 | Panic attacks | Yes |
| 5 | F | 40 | Panic attacks | Yes |
| 6 | F | 30 | Agoraphobia/Panic attacks | Yes |
| 7 | F | 28 | Agoraphobia/Panic attacks | No |
| 8 | F | 24 | Panic attacks | No |
| 9 | M | 34 | Panic attacks | Yes |

Conclusion

The investigators consider that ICS 205-930 reduces the "anticipatory" or "expectation anxiety" as well as the frequency and intensity of panic attacks. In four patients with decrease of energy, an increase in drive was observed. In contrast to diazepam, ICS 205-930 produced neither an immediate reduction of anxiety, nor a sedative effect nor a withdrawal effect. ICS was well tolerated and had no depressive potential.

TRIAL B

The study is a double-blind, randomized, placebo-controlled single center clinical trial in two parallel groups of patients with a diagnosis of panic attacks with or without agoraphobia.

Patients undergo medical and quantitative psychiatric examinations before the first dose (pre-medication evaluation) and weekly thereafter.

The first week is a pre-medication, screen-in phase as well as a wash-out period. The second study week is a single-blind placebo wash-out period. Following this period, 6 weeks of randomized treatment with either ICS 205-930 or placebo follow under double-blind conditions. Subsequently, patients are followed-up for a further 4 weeks; during this follow-up period, all patients receive placebo medication under single-blinded conditions for two weeks and nothing for the final two weeks.

Safety is determined by analysis and clinical interpretation of the following:

a) Physical examinations;

b) Vital signs;

c) Electrocardiogram;

d) Laboratory tests;

e) Adverse events;

f) Overall outcome assessment.

Efficacy is determined by analysis and clinical interpretation of the following:

a) Hamilton Anxiety Rating Scale;

b) Hamilton Depression Rating Scale;

c) Clinical Global Improvement Scale;

d) Patient self-ratings:

i) Disability Scale;

ii) Patient Global Improvements;

iii) Partnerschaftsfragebogen (PFB);

iv) Mobility Inventory;

v) Phobia Scale;

vi) Cognitive and Somatic Anxiety Scales;

vii) Hypochondriasis Scale;

viii) SCL-90;

ix) Patient diary.

TRIAL C

Trial A or B is repeated using another 5-$HT_3$ antagonist as defined above, e.g. GR 68755, or GR 38032 F, and similar results are obtained.

TRIAL D

In analogous manner to that described above in Trial A, B or C a clinical study is effected with patients suffering from agoraphobia.

Furthermore, it has been found that the 5-$HT_3$ receptor antagonists are also effective in preventing or treating obsessive compulsive disorders (OCD), as shown in clinical studies, for example in studies carried out in a method similar to those disclosed above and using a 5-$HT_3$ antagonist, e.g. ICS 205-930, GR 68 755 or GR 38 032 F.

The essential feature of obsessive compulsive disorder is recurrent obsessions or compulsions sufficiently severe to cause marked distress and/or significantly interfere with the person's normal routine, occupational functioning, usual social activities or relationships with others. Obsessions are persistent ideas, thoughts, impulses or images that are experienced, at least initially, as intrusive and senseless. Compulsions are repetitive, purposeful and intentional behaviors that are performed in response to an obsession, according to certain rules or in a stereotyped fashion. The behavior is designed to neutralize or to prevent discomfort or some dreaded event or situation. However, either the activity is not connected in a realistic way with what it is designed to neutralize or prevent, or it is clearly excessive. Frequently it may be associated with phobic avoidance of situations that involve the content of obsessions, such as dirt or contamination. For example, a person with obsessions about dirt may avoid public restrooms. In some cases of OCD, the obsession may become an overvalued idea or even an almost unshakable conviction.

A double-blind crossover placebo-controlled clinical trial using 20 in and out patients suffering from obsessive compulsive disorders as defined by DSM III R is effected in analogous manner to that described above with respect to Trial A, B, C or D. The study comprises e.g. a one week placebo run in period, 4 week treatment limbs and a one week washout period between treatments. A further week's placebo is administered, singleblind, after the second treatment limb. ICS 205-930 or another 5-$HT_3$ antagonist is used, e.g. using the dosages as indicated with respect to Trial A, B, C or D.

In a further or alternative embodiment the invention provides:

2. A method of treating a subject suffering from or prone to obsessive compulsive disorder, which comprises administering to a subject in need of such treatment a therapeutically effective amount of a 5-$HT_3$ receptor antagonist.

As alternatives to the above the present invention also provides:

3. A 5-$HT_3$ receptor antagonist for use in any method as defined under 1 and 2 above;

4. A 5-$HT_3$ receptor antagonist for use in the manufacture of a pharmaceutical composition for use in any method as defined under 1 and 2 above;

5. A composition for use in any method as defined under 1 and 2 above comprising a 5-$HT_3$ receptor antagonist together with one or more pharmaceutically acceptable diluents or carriers therefor.

For these indications, the appropriate dosage will, of course, vary depending upon, for example, the 5-$HT_3$ antagonist employed, the potency of the 5-$HT_3$ antagonist (e.g. as determined by in vitro, animal studies or the blister base forearm trial mentioned above), the host, the mode of administration and the nature and severity of the condition being treated.

The 5-$HT_3$ receptor antagonists are effective in treating panic attacks, relieving anticipatory anxiety and preventing panic states.

In general indicated dosages are of the same order as those used for chemotherapy induced emesis, e.g. about 0.1 to 50 mg per day.

For ICS 205-930 an indicated daily dosage for adult humans for use in the method of the invention is from about 0.5 to about 25 mg p.o., e.g. about 12.5 mg p.o or about 25 mg p.o.

The COMPOUNDS OF THE INVENTION may be administered in free base form or, when they can be formed, in pharmaceutically acceptable acid addition salt form, e.g. hydrochloride, or in a quaternary ammonium salt form. Such salts may be prepared in conventional manner and are in general known. They exhibit the same order of activity as the free base form.

The COMPOUNDS OF THE INVENTION may be administered by any conventional route, in particular enterally, preferably orally, e.g. in the form of tablets or capsules or parenterally, e.g. in the form of injectable solutions or suspensions.

Suitable pharmaceutical carriers and diluents for oral administration include polyethylene glycol, polyvinylpyrrolidone, mannitol, lactose etc. granulating agents, and disintegrating agents such as starch and alginic acid, binding agents such as stearic acid and gelatine, lubricating agents such as magnesium stearate, stearic acid and talc. Suspensions may contain conserving agents like ethyl p-hydroxybenzoate, suspending agents such as methyl-cellulose, tenside etc. For parenteral forms the compositions are preferably buffered, aqueous solutions (pH between 4 and 5).

The composition for use according to the invention may be prepared by bringing a 5-$HT_3$ receptor antagonist into intimate admixture with the pharmaceutically acceptable diluents or carriers and effecting formulation or presentation so as to provide for or permit convenient administration. Known galenic mixing procedures may be used, e.g. at room temperature or at a higher temperature which does not impair the stability of the active ingredients.

The following examples illustrate the invention.

EXAMPLE 1

Tablets for Oral Administration

Compound A is a 5-HT$_3$ antagonist and preferably ICS 205-930.

Tablets containing the constituents as specified below were produced in conventional manner and are used in the indications specified above.

| | |
|---|---|
| Compound A in form of hydrochloride (corresponding to 15 mg free base) | 16.9mg |
| Hydroxy-propyl-cellulose | 1.2mg |
| Corn Starch | 12.0mg |
| Lactose | 92.8mg |
| Silica | 0.6mg |
| Magnesium stearate | 1.5mg |
| Tablet weight | 125.0mg |

EXAMPLE 2

Injection Solution for I.V. Administration

A composition for injection is made up in conventional manner and is used e.g. at a dose of 10 mg a day.

| | A | B | C |
|---|---|---|---|
| Compound A in form of hydrochloride | 1.13[1] | 2.256[2] | 11.282[3] |
| Acetic acid (99 to 100%)* | 1.2 | 0.6 | 0.6 |
| Sodium acetate 3. H$_2$O* | 1.8 | 3.18 | 3.18 |
| Sodium chloride | 8 | 7.5 | 6.5 |
| Water for injection to | 1.0 ml | | |

[1] = 1 mg free base,
[2] = 2 mg free base,
[3] = 10 mg free base pH value 4.3;
*Buffer used 1/30 molar

EXAMPLE 3

Capsules for Oral Administration 5 mg and 15 mg capsules (A and B respectively) containing the constituents as specified below were produced in conventional manner and are used in the indications specified above 2-4 times a day in the case of A and once a day in the case of B.

| | A mg | B mg |
|---|---|---|
| Compound A in form of hydrochloride | 5.641 | 16.92 |
| Lactose 200 mesh | 84.929 | 79.29 |
| Lactose 100 mesh | 94.43 | 79.29 |
| Corn starch | 120.00 | 120.00 |
| Silica | 1.5 | 1.5 |
| Magnesium stearate | 3.0 | 3.0 |
| | 300 mg | 300 mg |

Capsules containing other weights can be formulated in conventional manner.

The active ingredients are intimately admixed employing conventional galenic procedures, filled into hard gelatin capsules and the capsules sealed.

COMPOUNDS OF THE INVENTION are well tolerated at dosages required for use in accordance with the present invention.

Pharmaceutically acceptable salt forms exhibit the same or similar levels of tolerability as the compounds in free form.

It is claimed:

1. A method of treating panic disorders, or obsessive compulsive disorders comprising administering to a subject in need of such treatment a therapeutically effective amount of a 5-HT$_3$ receptor antagonist, in free base or pharmaceutically acceptable acid addition or quaternary ammonium salt form.

2. A method according to claim 1 wherein the 5-HT$_3$ receptor antagonist is selected from the group consisting of:

1,2,3,9-tetrahydro-9-methyl-3-[(2-methyl-1H-imidazol-1-yl)-methyl]-4H-carbazol-4-one;

1-methyl-indazol-3-yl carboxylic acid 9-methyl-9-aza-bicyclo-[3.3.1]non-3α-yl amide;

zacopride, in optically active form or in racemic form;

trans-hexahydro-8-(3-indolylcarbonyloxy)-2,6-methano-2H-quinolizin- 3(4H)one;

benzo [b]thien-7-yl carboxylic acid endo-8-methyl-8-azabicyclo[3.2.1]oct-3-yl ester;

3-(5-methyl-1H-imidazol-4-yl)-1-(1-me thyl-1H-indol-3-yl)- 1-propanone;

1-methyl-indazol-3-yl carboxylic acid endo-8-methyl-8-azabicyclo[3.2.1oct-3-yl amide;

1,2,3,9- tetrahydro-9-methyl-3-(5-methyl-1H-imidazol-4-yl)-methyl- 4H-carbazol-4-one;

and the pharmaceutically acceptable acid addition salts of said compounds.

3. A method according to claim 1 wherein the 5-HT$_3$ receptor antagonist is selected from the group consisting of:

2,3,4,5-tetrahydro-5-(phenylmethyl)-2-[(5-methyl-1H-imidazol- 4-yl)methyl]-1H-pyridol[4,3,-b]indol-1-one;

5-cyclopentyl-2,3,4,5-tetrahydro-2-[(5-methyl-1H-imidazol-4-yl)methyl]-1H-pyridol[4,3-b]indol-1-one;

2,3,4,5-tetrahydro-2-[(5-methyl-1H-imidazol-4-yl)methyl-5-propyl- 1H-pyridol[4,3-b]indol-1-one, 5-(cyclopentylmethyl)-2,3,4,5-tetrahydro-2-[(5-methyl-1H-imidazol- 4-yl)methyl-1H-pyrido[4,3-b]indol-1-one;

3,4,5,6-tetrahydro-6-methyl-2-[(5-methyl-1H-imidazol-4-yl)methyl-azepino[4,3-b]indol-1-(2H)-one;

2,3,4,5-tetrahydro-N,N-dimethyl-2-[(5-methyl-1H-imidazol-4-yl)methyl- 1-oxo-5H-pyrido[4,3-b]indol-5-carboxamide 2,3,4,5-tetrahydro-2-[(5-methyl-1H-imidazol-4-yl)methyl-5-( 2-propynyl)-1H-pyridol[4,3-b]indol-1-one;

3-(5-methyl-1H-imidazol-4-yl)-1-(1-naphthalenyl)1-propanone;

1-(4-methoxy-1-naphthalenyl)-3-(5-methyl-! H-imidazol-4-yl)- 1-propanone, 1-(2-hydroxy-1-naphthalenyl)-3-(5-methyl-1H-imidazol-4-yl)-1-propanone, 1-(benzo[b]thien-3-yl)-3-(5-methyl-1H-imidazol-4-yl)-1-propanone, 3-(5-methyl-1H-imidazol-4-yl)-1-(1-methyl-1H-indazol-3-yl)- 1-propanone, 3-(5-methyl-1H-imidazol-4-yl)-1-(1-methyl-1H-indol-4-yl)-1-propanone;

1,2,3,9-tetrahydro-3-((1H-imidazol-2-yl)methyl-9-methyl-4H-carbazolone;

3-(1H-imidazol-2-yl)-1-(1-methyl-1H-indol-3-yl)-1-propanone;

3-(5-methyl-1H-imidazol-4-yl)-1-(1,7-dimethyl-1H-indol-3-yl)propanone;

3-(5-methyl-1H-imidazol-4-yl)-1-(1-methyl-1H-indol-3-yl)-1-propanone, 3-(5-methyl-1H-imidazol-4-yl)-1-(1,2-dimethyl-1H-indol-3-yl)-1-propanone, 2,3-dimethyl-3-(5-methyl-1H-imidazol-4-yl)-1-(1-methyl-1H-indole-3-yl)-1-propanone, N,1-dimethyl-7-fluoro-N-[(5-methyl-1H-imidazol-4-yl)methyl[-1H-indole-3-carboxamide, N,1-dimethyl-N-[(5-methyl-1H-imidazol-4-yl)methyl]-1-indole-3-carboxamide, 1-amino-5a,6,7,8,9,9a-hexahydrodibenzofuran-4-(N-1-azabicyclo-[2.2.2.]oct-3-yl)carboxamide;

2-chloro-5a,6,7,8,9,9a-hexahydrodibenzofuran-4-(N-1-azabicyclo-[2.2.2.]oct-3-yl)carboxamide;

1-amino-2-chloro-5a,6,7,8,9,9a-hexahydrodibenzofuran-4-(N-1-azabicyclo-[2.2.2.]oct-3-yl)carboxamide;

2-chloro-cis-5a,6,7,8,9,9a-hexahydrodibenzofuran-4-(N-1-azabicyclo-[2.2.2.]oct-3-yl)carboxamide;

2-chloro-cis-5aS,6,7,8,9,9aS-hexahydrodibenzofuran-4-(N-1-azabicyclo-[2.2.2.]oct-3S-yl)carboxamide;

2-chloro-cis-5aS,6,7,8,9,9.aS-hexahydrodibenzofuran-4-(N-1-azabicyclo-[2.2.2.]oct-3R-yl)carboxamide;

2-chloro-cis-5aR,6,7,8,9,9aR-hexahydrodibenzofuran-4-(N-1-azabicyclo-[2.2.2.]oct-3S-yl)carboxamide;

2-chloro-cis-5aR,6,7,8,9,9aR-hexahydrodibenzofuran-4-(N-1-azabicyclo-[2.2.2.]oct-3R-yl)carboxamide;

2-chloro-trans-5a,6,7,8,9,9a-hexahydrodibenzofuran-4-(N-1-azabicyclo-[2.2.2.]oct-3-yl)carboxamide;

5,6,9,10-tetrahydro-10-[(5-methyl-1H-imidazol-4-yl)methyl]-4H-pyrido[3,2,1-j,k]carbazol-11(8H)-one;

3,4-dihydro-2-[ (5-methyl-1H-imidazol-4-yl)methyl]-1(2H)-dibenzofuranone;

3,4-dihydro-2- [(5-methyl-1H-imidazol-4-yl)methyl]-1(2H)-dibenzothiophenone;

6,7,8,9-tetrahydro-5-methyl-9-[(2-methyl-1H-imidazol-1-yl)methyl]-cyclohept[b]indol-10( 5H)-one;

3,4-dihydro-2- [(5-methyl-1H-imidazol-4-yl)methyl]-benzofuro[3,2-c]pyridin-1(2H)-one, 3,4-dihydro-2-[(5-methyl-1H-imidazol-4-yl)methyl]-[1] benzothieno-[3,2-c]pyridin-1(2H)-one;

1,2-dihydro-3-[5-methyl-1H-imidazol-4-yl)methyl]-4(3H)phenanthrenone;

3,4-dihydro-2-[(5-methyl-1H-imidazol-4-yl)methyl]-benz[h]isoquinolin-1(2H)-one;

1-(5,6-dihydro-4H-pyrrolo[3,2,1-i,j]quinolin-1-yl)-3-(5-methyl- 1H-imidazol-4-yl)-1-propanone;

and the pharmaceutically acceptable acid addition salts of said compounds.

4. A method according to claim 1 wherein the 5-HT$_3$ receptor antagonist is indol-3-yl carboxylic acid endo-8-methyl- 8-aza-bicyclo[3.2.1]oct-3-yl ester, or a pharmaceutically acceptable acid addition salt thereof.

5. A method according to claim 1 wherein the 5-HT$_3$ receptor antagonist is administered in pharmaceutically acceptable acid addition salt form.

6. A method according to claim 4 wherein the compound is administered in pharmaceutically acceptable acid addition salt form.

7. A method according to claim 1 wherein the 5-HT$_3$ receptor antagonist is 1,2,3,9-tetrahydro-9-methyl-3-[(2-methyl-1H-imidazol-1-yl)methyl]-4H-carbazol-4-one, or a pharmaceutically acceptable acid addition salt thereof.

8. A method according to claim 7 wherein the compound is administered in pharmaceutically acceptable acid addition salt form.

* * * * *